United States Patent
Toyoshima et al.

(12)

(10) Patent No.: US 7,258,910 B2
(45) Date of Patent: *Aug. 21, 2007

(54) TOPSHEET FOR ABSORBENT ARTICLE

(75) Inventors: Yasuo Toyoshima, Haga-gun (JP);
Hiroko Sugiura, Haga-gun (JP);
Takanobu Miyamoto, Haga-gun (JP);
Wataru Saka, Haga-gun (JP); Shoichi Taneichi, Haga-gun (JP)

(73) Assignee: Kao Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/071,103

(22) Filed: Mar. 4, 2005

(65) Prior Publication Data

US 2005/0147798 A1 Jul. 7, 2005

Related U.S. Application Data

(62) Division of application No. 09/956,950, filed on Sep. 21, 2001, now Pat. No. 6,926,948.

(30) Foreign Application Priority Data

Sep. 22, 2000 (JP) .............................. 2000-289364

(51) Int. Cl.
*B32B 3/28* (2006.01)
*B32B 3/30* (2006.01)
*A61F 13/20* (2006.01)

(52) U.S. Cl. ................. 428/181; 428/182; 604/385.01; 604/385.101

(58) Field of Classification Search ................ 428/156, 428/172, 174, 181, 182; 604/385.01, 385.101
See application file for complete search history.

(56) References Cited

U.S. PATENT DOCUMENTS

| | | | |
|---|---|---|---|
| 2,029,370 A | 2/1936 | Heldenbrand | |
| 2,622,051 A | 12/1952 | Hermanson et al. | |
| 4,841,734 A | 6/1989 | Torrence | |
| 4,847,134 A | 7/1989 | Fahrenkrug et al. | |
| 5,558,924 A | 9/1996 | Chien et al. | |
| 5,871,836 A | 2/1999 | Schultink et al. | |
| 6,171,682 B1 | 1/2001 | Raidel et al. | |
| 6,432,094 B1 * | 8/2002 | Fujioka et al. | 604/385.01 |
| 6,926,948 B2 * | 8/2005 | Toyoshima et al. | 428/181 |
| 2001/0009711 A1 | 7/2001 | Latimer et al. | |

FOREIGN PATENT DOCUMENTS

CN 1193271 A 9/1998

(Continued)

OTHER PUBLICATIONS

JP 11-318983, Nov. 1999, machine translation.*

*Primary Examiner*—Donald J. Loney
(74) *Attorney, Agent, or Firm*—Birch, Stewart, Kolasch & Birch, LLP

(57) ABSTRACT

A topsheet for an absorbent article which has an uneven profile formed on a surface thereof to be brought into contact with a wearer's skin, the uneven profile being flexibly deformable in conformity to the contour of the wearer's body and to the wearer's movement, and depressions of the uneven profile being capable of trapping high-viscosity excreta thereby separating the high-viscosity excreta from the wearer's skin while an absorbent article having the topsheet is worn.

5 Claims, 3 Drawing Sheets

FOREIGN PATENT DOCUMENTS

| | | |
|---|---|---|
| CN | 1238173 A | 12/1999 |
| EP | 0529641 A1 | 3/1993 |
| EP | 1055403 A2 | 11/2000 |
| JP | 51-146584 A | 12/1976 |
| JP | 61-124667 A | 6/1986 |
| JP | 63-296936 A | 12/1988 |
| JP | 63-309657 A | 12/1988 |
| JP | 2-133641 A | 5/1990 |
| JP | 5-59801 A | 3/1993 |
| JP | 7-232409 A | 9/1995 |
| JP | 8-3850 A | 1/1996 |
| JP | 8-246322 A | 9/1996 |
| JP | 8-302555 A | 11/1996 |
| JP | 10-502000 | 2/1998 |
| JP | 10-80445 A | 3/1998 |
| JP | 11-347062 | 12/1999 |
| JP | 2000-271170 A | 10/2000 |
| JP | 2002-65737 A | 3/2002 |
| WO | WO96/00545 | 1/1996 |
| WO | WO97/00656 A1 | 1/1997 |

\* cited by examiner

TOPSHEET FOR ABSORBENT ARTICLE

This application is a Divisional of application Ser. No. 09/956,950, filed on Sep. 21, 2001, now U.S. Pat. No. 6,926,948 and for which priority is claimed under 35 U.S.C. § 120; and this application claims priority of Application No. 2000-289364 filed in Japan on Sep. 22, 2000 under 35 U.S.C. § 119; the entire contents of all are hereby incorporated by reference.

FIELD OF THE INVENTION

The present invention relates to a topsheet for absorbent articles such as disposable diapers, sanitary napkins, and incontinence pads.

BACKGROUND OF THE INVENTION

Topsheets that have been used in absorbent articles, such as disposable diapers and sanitary napkins, include nonwoven fabrics prepared by various methods, perforated nonwoven fabrics, and perforated films of organic resins such as polyethylene.

Characteristics primarily required of absorbent articles include absorption characteristics relating to absorbing performance and surface characteristics for giving no adverse influences to the wearer's skin, such as an itch and a rash.

Conventional topsheets have satisfied the requirements for the absorption characteristics to some extent in letting low-viscosity waste liquids pass through and be absorbed quickly by an absorbent member lying under the topsheet but still leave room for improvement on the properties of making high-viscosity waste matter pass through and be absorbed. With respect to the surface characteristics for having no adverse influences on the skin, further improvements have been desired for alleviating skin irritation.

Skin troubles by absorbent articles are assumed attributed to the following causes. An absorbent article, while worn, creates an internal environment in which the skin is apt to be hydrated and swollen because of temperature and humidity rises, adhesion and remaining of the waste, e.g., urine or blood, and the like. The skin in such a condition is readily susceptible to physical irritation, i.e., the friction of the topsheet against the skin, and chemical irritation, namely, percutaneous absorption of irritants such as urine, soft stools or blood, resulting in skin troubles. It seems that the physical irritation is largely dependent on the surface characteristics of the topsheet with which the wearer's skin is in direct contact, and the chemical irritation is ascribable chiefly to high-viscosity waste that is less absorbable and likely to remain on the topsheet.

Under these circumstances, studies have been made to develop a topsheet for absorbent articles which feels soft.

JP-W-10-502000 (unexamined published international patent application) discloses a topsheet having a large number of protrusions extending along its longitudinal direction to have a wavy profile. The protrusions extending in the longitudinal direction contribute to soft feel but fail to retain their shape, being easily collapsed under the pressure while worn. More specifically, because the protrusions have a protuberant mountain-like profile, sticking out from the base (fixed part between adjacent projections), they have poor resistance against compression. As the protrusions are collapsed more and more, the contact area between the protrusions and the skin increases considerably. Therefore, they are not expected to suppress discomfort (overhydration) or skin troubles such as a rash. In addition, the protrusions having such a profile have limited conformability to the movement of the wearer's body. Due to the increase in contact area with the skin and the limited conformability, it is very likely that the topsheet causes friction on the skin, resulting in a failure to maintain the advantage of the wavy unevenness, i.e., soft feel, as designed.

JP-A-11-347062 discloses a topsheet having unevenness made by heat embossing. However, the top of the bosses are in a flat film form, the flat tops are hard and ruin the softness of the whole sheet.

Hence, the topsheets of related art do not have such protrusions that are flexible and deformable as would follow the body movement. A topsheet which securely prevents an itch, a rash, etc. while giving a wearer comfort of softness has not yet been provided.

SUMMARY OF THE INVENTION

An object of the present invention is to provide a topsheet for an absorbent article which maintains a macroscopic surface profile capable of making irritating body waste such as urine, soft tools and blood, particularly high-viscosity waste be absorbed quickly by an absorbent member without allowing the waste to remain on the surface thereof and yet which feels soft and gives little frictional irritation to the skin, hardly causing skin troubles, such as an itch and a rash.

The present invention accomplishes the above object by providing a topsheet for an absorbent article which has an uneven profile formed on a surface thereof to be brought into contact with a wearer's skin, the uneven profile being flexibly deformable in conformity to the contour of the wearer's body and to the wearer's movement, and depressions of the uneven profile being capable of trapping high-viscosity excreta thereby separating the high-viscosity excreta from the wearer's skin while an absorbent article having the topsheet is worn.

BRIEF DESCRIPTION OF THE DRAWINGS

The present invention will be more particularly described with reference to the accompanying drawings, in which.

DETAILED DESCRIPTION OF THE PREFERRED EMBODIMENTS

The present invention will be described in greater detail with reference to its preferred embodiments.

Figure 1:
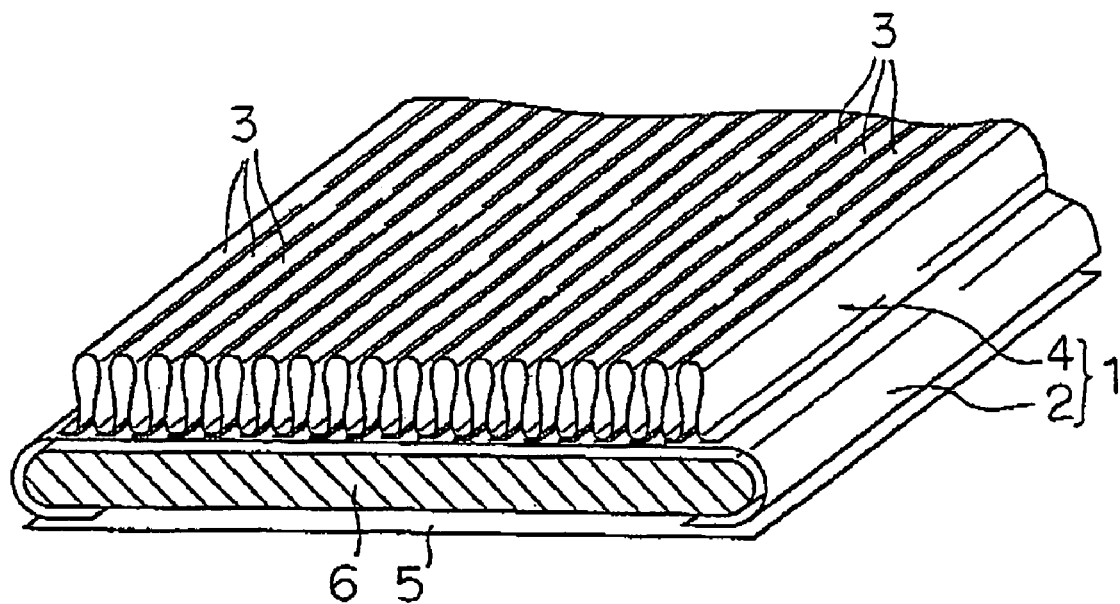
FIG. 1 is a perspective view of a part of a sanitary napkin in which a topsheet according an embodiment of the present invention is used.

FIG. 1 shows a topsheet 1 according to an embodiment of the present invention which is used in a sanitary napkin as an absorbent article.

Figure 2:
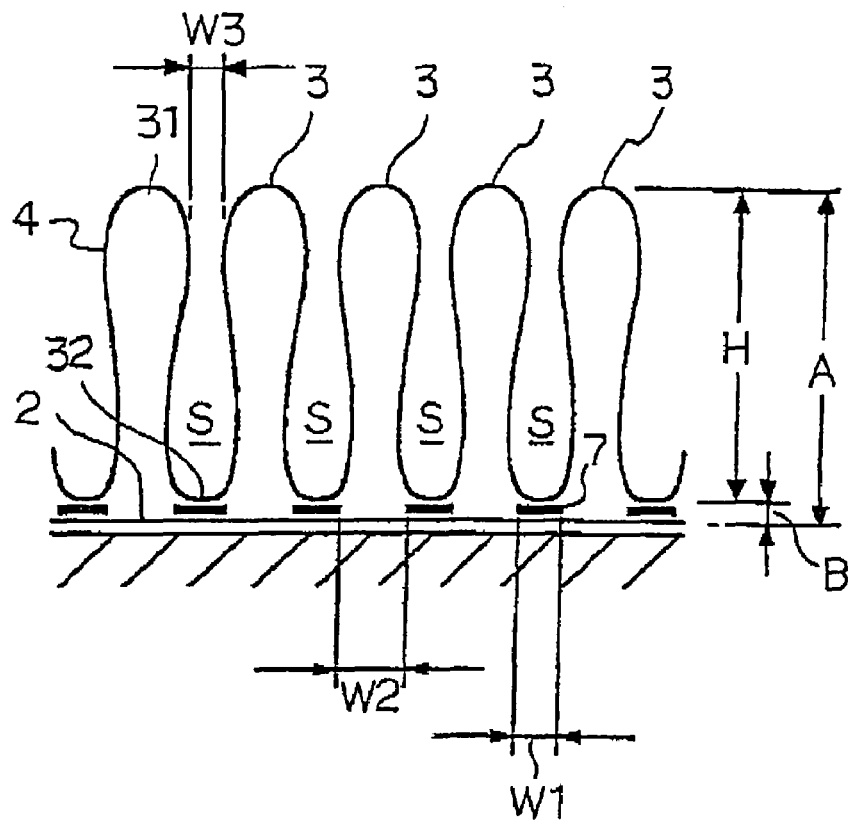
FIG. 2 is a schematic enlarged cross-sectional view of the uneven surface profile of the topsheet shown in FIG. 1.

As shown in FIGS. 1 and 2, the topsheet 1 has an uneven profile on its side to be brought into contact with wearer' skin (opposite to the side facing an absorbent member 6).

The uneven profile according to this embodiment is made up of a large number of parallel folds 3 formed of an unevenness-forming sheet 4 and joined to a base sheet 2. More specifically, an unevenness-forming sheet 4 is gathered into a great number of parallel folds 3 and joined to the base sheet 2 at the bases of the folds 3 in linear contact. As far as this embodiment is concerned, the unevenness-forming sheet 4 before being folded will be referred to as a folding sheet 4, while after being folded will be referred to as a folded sheet 4. The sanitary napkin comprises the topsheet 1 as a liquid-permeable sheet, a liquid-impermeable backsheet 5, and a liquid-retentive absorbent member 6 interposed between the topsheet 1 and the backsheet 5. The topsheet 1 is disposed with the longitudinal direction of the folds 3 agreeing with the longitudinal direction of the sanitary napkin.

The topsheet for absorbent articles according to the present invention is flexibly deformable in conformity to the contour of a wearer's body and to wearer's movement while in contact with the wearer's skin as a topsheet of an absorbent article. Further, the depressions of the uneven profile are capable of trapping high-viscosity excreta thereby separating the high-viscosity excreta from the wearer's skin.

A topsheet simply having an uneven profile on its surface on the wearer's side without flexible deformability to the contour or movement of a wearer's body will cause frictional irritation against the skin (physical irritation), not only giving a wearer discomfort but also causing skin troubles such as an itch and a rash.

If the depressions of an uneven profile are incapable of trapping high-viscosity excreta, contacts between high-viscosity excreta and the skin are not broken, and chemical irritation is given to the skin, which can cause skin troubles.

Even though the depressions of an uneven profile are capable of trapping high-viscosity excreta, if they are incapable of separating the trapped high-viscosity excreta from the wearer's skin, the high-viscosity excreta once trapped would leak when the topsheet is compressed under a strong force.

The expression "capable of separating high-viscosity excreta from the skin" is intended to mean that the topsheet traps high-viscosity excreta in its depressions which hardly come into contact with the skin without allowing the high-viscosity excreta to remain on at least the parts in contact with the skin (i.e., the tops of the unevenness) and also accelerates migration of the excreta to an absorbent member. The term "high-viscosity excreta" as used herein is intended to include liquid waste having a low viscosity of about 5 to 30 cps to solid waste having too high viscosities to be measured with a viscometer. As described later, a viscous liquid having a viscosity of 10,000 to 30,000 cps was used for evaluating the performance of a topsheet.

In order for the topsheet of the present invention to satisfy the above-mentioned requirements, the profile of the unevenness formed on the surface that comes in contact with a wearer's skin (hereinafter referred to as a surface profile) is preferably such that the height H measured from the top 31 to the base 32 (see FIG. 2) is 0.5 to 15 mm, particularly 1 to 10 mm.

If the height H is less than 0.5 mm, the size of the high-viscosity excreta-trapping space formed by the unevenness (the space between adjacent folds 3 and 3 in this embodiment) is insufficient, and it is difficult to quickly put high-viscosity excreta discharged on the topsheet into a state kept off the skin. If the height H exceeds 15 mm, the topsheet 1 hardly maintains the surface profile, resulting in impairment of flexibility and difficulty in trapping high-viscosity excreta in the depressions. The height H from the top 31 to the base 32 is obtained by subtracting the thickness of the topsheet at the base 32 (denoted as B in FIG. 2) as measured in the cross-sectional photograph from the thickness of the topsheet at the top 31 (denoted as A in FIG. 2), i.e., the initial thickness $L_0$, under a load of 0.5 gf/cm$^2$.

Means for making the uneven profile of the topsheet capable of flexible deformation in conformity to the contour and the movement of a wearer's body include fulfillment of the following conditions (1) and (2) (hereinafter inclusively referred to as conditions for flexibility).

(1) When the topsheet is compressed in the thickness direction under a load increasing up to 20 gf/cm$^2$, the maximum thickness change for a load increase by $\Delta 2.5$ gf/m$^2$ is 0.3 to 5 mm, particularly 0.5 to 4 mm.

(2) A compressive deformation percentage under 20 gf/cm$^2$ load ($C\Delta L_{20}$) is 50 to 90%, particularly 60 to 90%, as calculated from the equation: $C\Delta L_{20}=(L_0-L_{20})/L_0\times 100$, wherein $L_0$ is the initial thickness of the topsheet, and $L_{20}$ is the thickness of the topsheet under a load of 20 gf/cm$^2$. The term "initial thickness" as used herein means the thickness under a load of 0.5 gf/cm$^2$.

The pressure imposed on an absorbent article, for example, a sanitary napkin while worn seems to vary widely because, for one thing, the part of a wearer's body to which the absorbent article is applied has a complicatedly curved contour, which changes greatly with wearer's movement and, for another, the style of wearing a sanitary napkin, i.e., the kind of panties and whether a girdle is used, varies among wearers depending on the length of their period and the amount of menstrual blood. In such a situation, a pressure change of $\Delta 2.5$ gf/cm$^2$ and application of a 20 gf/cm$^2$ load are within ranges that are typically and/or commonly encountered.

With the maximum thickness change for a load change of $\Delta 2.5$ gf/cm$^2$ ranging from 0.3 to 5 mm, the topsheet is smoothly deformed with no resistance against pressure by the skin, causing little frictional irritation to the skin. As a result, the topsheet feels comfortable and effectively prevents development of skin troubles.

If the maximum thickness change for a load change of $\Delta 2.5$ gf/cm$^2$ is less than 0.3 mm, conformability of the topsheet to the body's movement is poor and may give excessive frictional irritation to the skin. If the maximum thickness change is more than 5 mm, the topsheet tends to be too soft to maintain the surface profile, failing to trap high-viscosity excreta in the depressions.

A topsheet having a higher compressive deformation percentage under 20 gf/cm$^2$ load ($C\Delta L_{20}$) comes into contact with the skin more softly. From considerations particularly for the vulva, which is depressed, the topsheet which is deformable softly under a pressure no higher than 20 gf/cm$^2$ would cause little irritation. If the compressive deformation percentage $C\Delta L_{20}$ is less than 50%, the topsheet has high resistance to the skin. If it is more than 90%, it is likely that the topsheet is too soft to maintain its surface profile, failing to trap high-viscosity excreta in the depressions.

It is not the entire area of the topsheet but only the tops 31 of the surface profile and their vicinities that come into contact with the skin. Therefore, the contact area with the skin is remarkably reduced. Further, spaces S of prescribed configuration formed among protrusions or in the folds (in the folds in the embodiment shown in FIG. 1) are retained satisfactorily so that high-viscosity excreta are swiftly entrapped therein and separated from the skin.

It is preferred for at least part of the topsheet that is brought into contact with the excreting part of a wearer's body to fulfill at least one of the following conditions (3) and (4) (hereinafter referred to as conditions for shape retention) in order that the uneven profile may be deformed softly in conformity to the contour and the movement of the body and that high-viscosity excreta may be trapped satisfactorily in the depressions of the uneven profile.

(3) When the topsheet is compressed in the thickness direction under a load increasing up to 20 gf/cm², a compressive deformation percentage under 2.5 gf/cm² load ($C\Delta L_{2.5}$) is 0.1 to 5%, particularly 0.1 to 4%, as calculated from the equation: $C\Delta L_{2.5}=(L_0-L_{2.5})/L_0\times100$, wherein $L_0$ is the initial thickness of the topsheet, and $L_{2.5}$ is the thickness of the topsheet under a load of 2.5 gf/cm².

The compressive deformation percentage $C\Delta L_{2.5}$ being within the above range, the protrusions of the uneven profile hardly collapse in the initial stage of compression, i.e., under a low applied pressure. As a result, the high-viscosity excreta trapping performance is improved, and high-viscosity excreta can be separated from the skin.

(4) The compressive deformation percentage under a 5 gf/cm² load ($C\Delta L_5$) is 5 to 20%, particularly 5 to 15%, as calculated from the equation: $C\Delta L_5=(L_0-L_5)/L_0\times100$, wherein $L_0$ is the initial thickness of the topsheet, and $L_5$ is the thickness of the topsheet under a load of 5 gf/cm² in the step of the topsheet compression.

With the compressive deformation percentage $C\Delta L_5$ falling within the above range, the high-viscosity excreta trapping performance is improved further. Fulfillment of the condition (4) is also effective in reducing skin irritation by friction.

It is still preferred for the topsheet to satisfy the following condition (5) in order that the uneven profile may be deformed flexibly in conformity to the contour and the movement of a wearer's body and that high-viscosity excreta trapped in the depressions of the uneven profile may be separated from the skin more securely.

(5) When the topsheet is compressed under a load increasing up to 2.5 gf/cm² to a thickness $L_{2.5}$, further compressed by increasing the load to 20 gf/cm², and relieved from compression until the load is reduced to 2.5 gf/cm², the topsheet has a compressive recovery ($D\Delta L_{R2.5}/L_{2.5}$) of 70% or more, particularly 80 to 100%, as obtained from the thickness $L_{2.5}$ and the thickness after the relief ($L_{R2.5}$) according to the equation: $D\Delta L_{R2.5}/L_{2.5}=L_{R2.5}/L_{2.5}\times100$.

The compressive recovery $L_{R2.5}/L_{2.5}$ being in the above range means particularly excellent conformability of the surface profile to the movement of a wearer's body. Fulfillment of the condition (5) promises satisfactory retention of the surface structure capable of trapping high-viscosity excreta and flexible deformability for reduction of skin irritation while the absorbent article is used.

The topsheet of the present invention which shows the maximum thickness change with a load change of $\Delta 2.5$ gf/cm² at the very start of compression, i.e., when the load imposed rises from zero to 2.5 gf/cm², can be seen as capable of achieving the object of reducing friction against the skin, one of the objects contemplated in the present invention. However, from the viewpoint of fulfillment of the above-mentioned conditions for shape retention, it is desirable that the maximum thickness change with a load change of $\Delta 2.5$ gf/cm² should occur while the load is increased from 2.5 gf/cm² up to 20 gf/cm².

The above-described compression characteristics, i.e., a thickness change for a load change $\Delta 2.5$ gf/cm², the maximum of thickness changes, compressive deformation percentages under 2.5 gf/cm², 5 gf/cm² and 20 gf/cm² ($C\Delta L_{2.5}$, $C\Delta L_5$, and $C\Delta L_{20}$), and a recovery from compressive deformation ($D\Delta L_{R2.5}/L_{2.5}=L_{R2.5}/L_{2.5}\times100$) are measured as follows.

Measurement of Compression Characteristics:

The compression characteristics can be measured with a compression tester KES-FB3, supplied by Katotec. The tester has a disk indenter having a compressing area of 2 cm². The disk indenter is vertically moved to give a compression-recovery load to such a sample as fabric or film to obtain a compression load-compressive deformation hysteresis loop for the compression-recovery cycle, which furnishes compression data, such as the sample thickness, the compression work done, the recovery properties and the like.

In carrying out the measurement on the topsheet, a 2.5 cm-side square cut out of the topsheet is set on KES-FB3. The disk indenter is moved down at a speed of 0.02 mm/sec to apply a compression load up to 20 gf/cm², at which time the manual return switch is pushed to switch the downward movement to an upward movement. The disk indenter is lifted until the load decreases to zero. Thus, a hysteresis loop for the compression-recovery cycle is obtained.

A thickness reduction for every load increase by 2.5 gf/cm² is obtained from the hysteresis loop. The thickness reduction (mm) in the load range in which the test piece has undergone the greatest thickness change is taken as the maximum thickness change for a load change $\Delta 2.5$ gf/cm².

Further, the thicknesses $L_0$, $L_{2.5}$, $L_5$ and $L_{20}$ at 0.5 gf/cm², 2.5 gf/cm², 5 gf/cm² and 20 gf/cm², respectively, in the compression step are read from the hysteresis loop to calculate the compressive deformation percentages $C\Delta L_{2.5}$, $C\Delta L_5$ and $C\Delta L_{20}$ at the respective loads.

The compressive deformation recovery ($D\Delta L_{R2.5}/L_{2.5}$) is calculated from the thickness $L_{2.5}$ at 2.5 gf/cm² in the compression step and the thickness $L_{R2.5}$ at 2.5 gf/cm² in the recovery step according to the equation: $D\Delta L_{R2.5}/L_{2.5}=L_{R2.5}/L_{2.5}\times100$.

The topsheet of the present invention preferably has the following configuration so as to satisfy the conditions (1) to (5). Joints 7 between the folded sheet 4 and the base sheet 2 each have a width W1 (see FIG. 2) of 0.1 to 10 mm, particularly 0.5 to 5 mm, and are regularly spaced at an interval W2 (see FIG. 2) of 1 to 30 mm, particularly 2 to 15 mm. The minimum distance W3 (see FIG. 2) between adjacent folds 3 is 0 to 5 mm, particularly 0 to 3 mm, as measured under no load applied. The minimum distance W3 of 0 mm means that adjacent folds 3 and 3 are in contact with each other.

While the folded sheet 4 is joined to the base sheet 2 via an adhesive applied on the base sheet 2 in parallel with the folds 3 at a prescribed interval in the embodiment shown in FIG. 2, joining with an adhesive can be replaced with other known means, such as heat sealing and ultraviolet sealing.

It is preferred for each fold 3 formed of the folding sheet 4 to have an Ω-shaped cross-sectional contour (profile) in its width direction as shown in FIG. 2. The term "Ω-shape" is intended to mean a shape which, when divided into an upper half and a lower half, has the maximum width in the upper half and a neck which is narrower than the maximum width in the lower half.

Since the individual folds to have a Ω-shaped contour in the width direction this provides a structure in which the expanded part of the upper half is supported by the narrowed part of the lower half, which is ready to meet the conditions for shape retention.

For forming folds having a particularly favorable Ω-shaped transverse section, it is desirable for the folding sheet 4 to have a bulk softness of 5 to 40 cN, particularly 15 to 30 cN. The "bulk softness" as referred to herein is measured as follows.

Measurement of Bulk Softness:

A 30 mm wide and 150 mm long test piece cut out of a sample sheet is looped with the shorter sides overlapped. The upper and lower ends of the overlap are stapled in parallel with the circumferential direction with No. 10-1M staples available from Max Co., Ltd. to make a cylindrical specimen having a diameter of 45 mm and a height of 30 mm. The cylindrical specimen is set upright on a Tensilon compression tester RTA-100, supplied by Orientec K.K., and compressed in its axial direction by a disk having a diameter of 70 mm or more at a speed of 10 mm/min. The maximum load applied in the compression is read. The initial position of the compressing disk is higher than the height of the specimen (30 mm). The measurement was made on five specimens for each sample sheet to obtain an average.

The folding sheet 4 has two bulk softness values, one in the direction which agrees with the longitudinal direction of the folds 3 of the folded sheet 4, and the other in the direction which agrees with the width direction of the folds 3. It is preferred for the folding sheet 4 to have its bulk softness in the direction agreeing with the width direction of the folds 3 range within the above range. The bulk softness in the direction agreeing with the width direction of the folds 3 is measured by preparing a cylindrical specimen whose circumferential direction agrees with the longitudinal direction of the folds 3.

Materials of the folding sheet 4 used in the topsheet 1 according to the present embodiment include nonwoven fabric made of single or conjugate fiber of polyethylene, polypropylene, polyester, etc.; perforated and thereby liquid-permeable film of polyethylene, etc.; and composites of nonwoven fabric and a film.

The base sheet 2 can be of any material that is commonly employed in general absorbent articles with no particular restriction.

It is preferred that the surface unevenness be formed on at least the area corresponding to the excreting part of a wearer's body, particularly over the total area of the topsheet disposed on the absorbent member. Because the uneven surface profile is effective in preventing leaks of body fluids flowing on the surface of the topsheet, in another embodiment there is disposed the uneven surface profile in the area corresponding to the whole peripheral portion of the absorbent member.

The unevenness of the topsheet may be made up of a great number of protrusions having a nipple-like shape or any other shapes.

Another embodiment of the topsheet according to the present invention will be described by referring to FIGS. 4 and 5.

Figure 4:
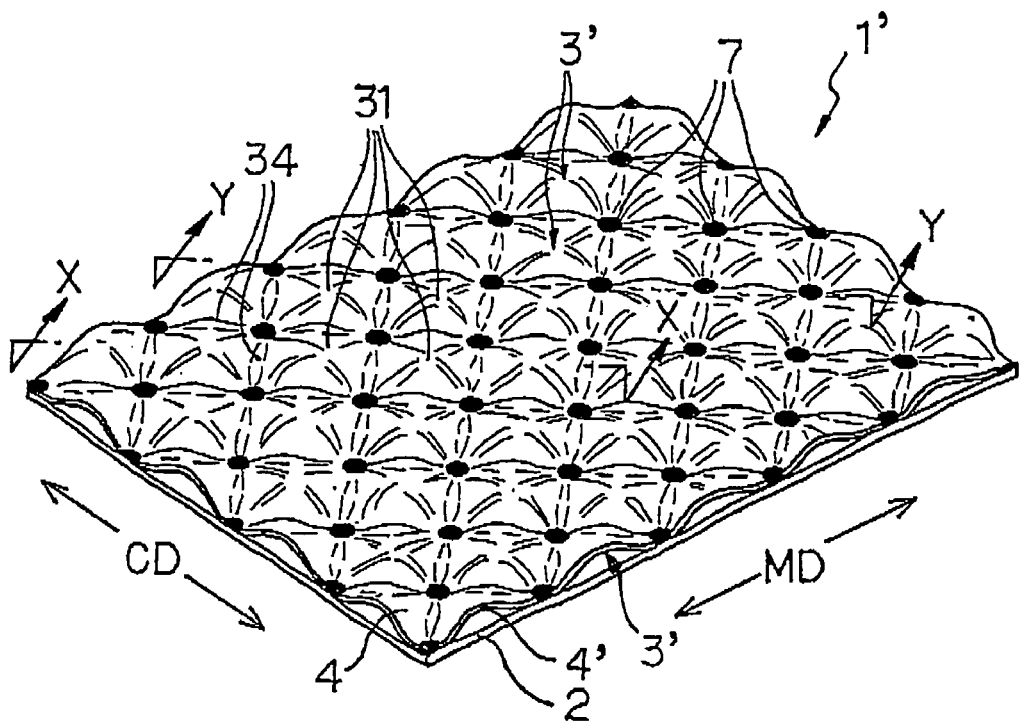
FIG. 4 is a schematic perspective view of a topsheet according to another embodiment of the present invention.

The topsheet 1' shown in FIG. 4 is composed of an uneven sheet 4' and a base sheet 2. The uneven sheet 4' and the base sheet 2 are superposed on each other thermally fusion-bonded in parts (at joints 7) by heat embossing in a prescribed pattern. The uneven sheet 4' forms a large number of bulges 3' protruding toward the wearer's skin while worn (hereinafter referred to as protrusions 3') arrayed in both the machine direction (MD) and the cross direction (CD).

Figure 5A:
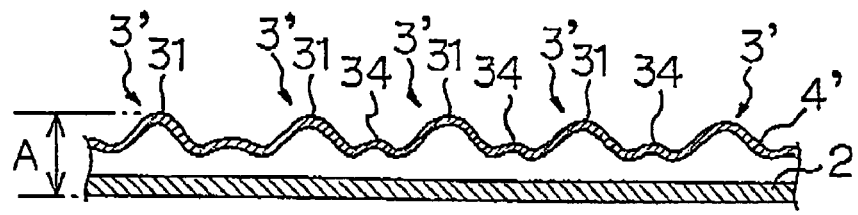
FIG. 5A is a cross-section along X-X line of FIG. 4.
Figure 5B:
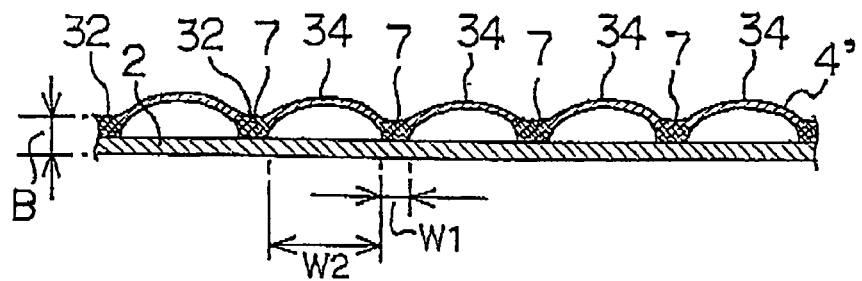
FIG. 5B is a cross-section along Y-Y line of FIG. 4.

The uneven sheet 4' is nonwoven fabric, and the base sheet 2 is a fiber web having been thermally shrunken. As shown in FIGS. 5A and 5B, the uneven sheet 4' separates from the base sheet 2 at at least the sites forming the top 31 of the protrusions 3'. Specifically, the uneven sheet 4' separates from the base sheet 2 over substantially the entire area thereof except the joints 7 with the base sheet 2.

As shown in FIGS. 5A and 5B, the uneven sheet 4' also has protrusions 34 which are smaller and lower than the protrusions 3' on the borders between every adjacent protrusions 3'. A vertical cross-section of the uneven sheet 4' taken along a line that does not contain any joint 7, namely, a straight line that connects tops 31 of any adjacent protrusions 3' via the smaller protrusion 34 on the border therebetween (X-X line in FIG. 4) has a continuous curved and almost wavy profile as shown in FIG. 5A. This wavy profile is made up of the contour of the top 31 of protrusions 3' and its vicinities, the contour of the smaller protrusions 34, and the contour of depressed borders connecting the protrusions 3' and 34. A vertical cross-section of the uneven sheet 4' taken along a line that contains joints 7 (Y-Y line in FIG. 4) is shown in FIG. 5B. The uneven sheet 4' does not always need to have the smaller protrusions 34 on the borders between adjacent protrusions 3' and 3'. In this case, the vertical cross-section along a line that does not contain any joint 7 has an almost wavy profile in which the contour of the tops 31 of protrusions 3' and their vicinities and the contour of depressed or flat borders alternate.

Figure 6:
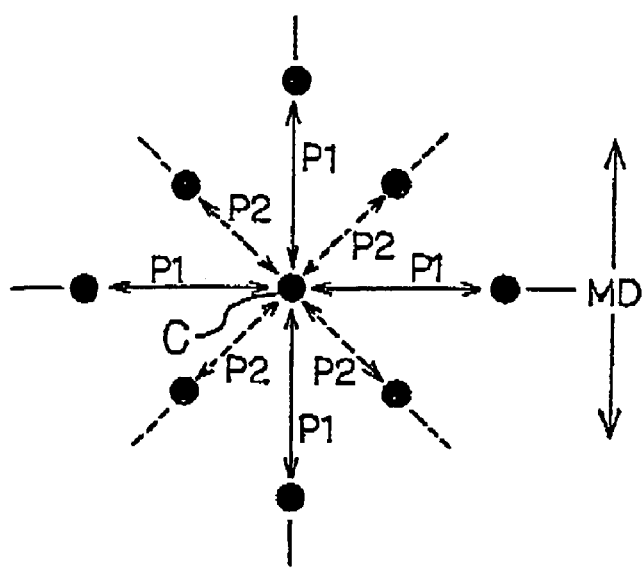
FIG. 6 is a plan view of the embossing pattern used in the preparation of the topsheet shown in FIG. 4.

The topsheet 1' according to the embodiment shown in FIG. 4 can be obtained by superposing an unevenness-forming sheet 4 (a sheet before forming unevenness) and a base sheet 2, embossing the two sheets to give the embossed pattern shown in FIG. 6 and then thermally shrinking only the base sheet 2. The embossed pattern has two different pitches P1 and P2 (P1>P2) in terms of distance between centers of adjacent standing pins. The protrusions 3' are formed at pitch P1, while the smaller protrusions 34 are formed at pitch P2.

The protrusions 3' preferably have a height H (the distance from the top 31 to the base 32 (A-B), wherein A is measured under a load of 0.5 gf/cm$^2$) is 0.5 to 15 mm, particularly 0.5 to 7 mm as measured under a load of 0.5 gf/cm$^2$. The joints 7 preferably have a width W1 of 0.1 to 10 mm, particularly 0.5 to 5 mm. The interval W2 between adjacent joints 7 is preferably 0.5 to 20 mm, still preferably 0.5 to 10 mm.

The above-described surface unevenness having a continuous wavy profile achieves a high compressive deformation percentage. It provides a soft texture as well as a good fit because of flexible deformability in conformity to a wearer's movement. In particular, the continuous smaller protrusions 34 protruding from the depressed borders actively bear a part in deformation and/or recovery. Further, the continuous protrusions 3' which are further outward over the smaller protrusions 34 have such a structure as easily retains their height even under pressure, thereby securing spaces for entrapping high-viscosity excreta. Thus, the topsheet 1' is capable of softly following the movement of a wearer's body and trapping high-viscosity excreta.

The unevenness-forming sheet 4 used in this embodiment may be replaced with a fiber web to make a topsheet having protrusions filled with fibers. Joining of the unevenness-forming sheet 4 and the base sheet 2 by thermal embossing can be replaced with joining with an adhesive.

Where a fiber web is used as an unevenness-forming sheet 4, each joint 7 between the unevenness-forming sheet 4 and the base sheet 2 preferably has a width W1 of 0.1 to 10 mm, particularly 0.5 to 5 mm. The interval W2 between adjacent joints 7 is preferably 0.5 to 20 mm, still preferably 0.5 to 10 mm. The minimum distance between adjacent protrusions 3' is preferably 0 to 5 mm, particularly 0 to 3 mm, as measured under no load applied.

The uneven sheet 4' may have a large number of slits of prescribed length.

The absorbent articles to which the topsheet of the present invention is applicable include not only sanitary napkins but panty liners, disposable diapers, incontinence pads, and so forth.

The present invention will now be illustrated in greater detail with reference to Examples. Unless otherwise noted, all the percents and ratios are given by weight.

Preparation of Sample G:

A topsheet having the configuration of FIG. 1 was prepared by using a nonwoven fabric sheet made of 60/40 mixed fiber of polyethylene and polyester and having a basis weight of 25 g/m$^2$, an initial thickness (at 0.5 gf/cm$^2$) of 0.4 mm and a bulk softness of 16 cN in the MD and 18 cN in the CD as a base sheet 2 and a folding sheet (unevenness-forming sheet) 4. An adhesive was applied to the base sheet 2 in a pattern of streaks, and the folding sheet 4, as folded, was joined to the base sheet 2 via the adhesive to form joints having a width W1 of 1 mm at a regular interval W2 of 1 mm. The folds 3 of the folded sheet 4 had an Ω-shaped contour having a height H of 5.2 mm. The minimum distance between adjacent folds 3 was 0.3 mm. The topsheet had an initial thickness (at 0.5 gf/cm$^2$) of 5.6 mm.

Compression characteristics of the resulting topsheet, designated sample G, are shown in Table 1 below.

Preparation of Sample H:

A nonwoven fabric sheet (spun-bond nonwoven) made of polypropylene fiber and having a basis weight of 12 g/m$^2$, an initial thickness (at 0.5 gf/cm$^2$) of 0.15 mm, and a bulk softness of 3.7 cN in the MD and 3.3 cN in the CD was used as an unevenness-forming sheet 4. Crimping fibers capable of crimping in a helix (CPP fiber, available from Daiwabo Co., Ltd.; 2.2 dtex×51 mm) were fabricated by carding into a web having a basis weight of 35 g/m$^2$, which was used as a base sheet 2.

The unevenness-forming sheet 4 and the base sheet 2 were heat-sealed together by thermal embossing at 220° C. using an embossing plate having standing pins (diameter: 1.5 mm) in a regularly repeated pattern. As shown in FIG. 6, a unit pattern of the pins is made up of 9 pins; a center pin, two pins adjacent to the center pin arranged in the MD at a center-to-center distance (P1) of about 7 mm, two pins adjacent to the center pin arranged in the CD at a center-to-center distance (P1) of about 7 mm, and four pins arranged on two lines passing through the center pin making 45° with MD or CD at a center-to-center distance (P2) of about 5 mm.

The resulting embossed laminate was allowed to stand in a hot drier at 130° C. for at least 10 minutes to make the base sheet 2 shrink in the horizontal direction to obtain a topsheet 1' having the configuration shown in FIGS. 4, 5A and 5B.

The resulting topsheet 1' had a great number of protrusions 3' in both the MD and the CD, each protrusion 3' having a height H (the distance from the top 31 to the base 32 (A-B), wherein A is measured under a load of 0.5 gf/cm$^2$) of 1.5 mm. The compression characteristics of the topsheet 1', designated sample H, are shown in Table 1.

For comparison, compression characteristics of samples A to F shown below were measured. The results obtained are shown in Table 1. Samples A to C are perforated polyethylene films typically available in the market as a topsheet of absorbent articles. Samples D and E are commercially available topsheets comprising nonwoven fabric. Samples B, C and E had an almost flat surface.

Sample A:

A perforated film topsheet used in a sanitary napkin Laurier Dry Up Mesh Regular, available from Kao Corp. (sales name: Laurier DR-h-114)

Sample B:

A perforated film topsheet used in a sanitary napkin Whisper Regular, available from the Procter & Gamble Co. (sales name: Whisper Ca5-a)

Sample C:

A perforated film topsheet used in a sanitary napkin Elis Sarasara Silk Regular, available from Daio Paper Corp. (sales name: Elis SS-R2)

Sample D:

A perforated nonwoven fabric topsheet used in a sanitary napkin Laurier Yawaraka Mesh Slim, available from Kao Corp. (sales name: Laurier UN-f-114)

Sample E:

A topsheet (Cotton Fuwafuwa Sheet) used in a sanitary napkin Sofy Bodyfit (for medium to long-time use), available from Uni-Charm Corp. (sales name: Sofy aon). The topsheet was sampled as joined to nonwoven fabric which is disposed under the topsheet and perforated together with the topsheet.

Sample F:

A nonwoven fabric sheet (spun-bond nonwoven) made of polypropylene fiber and having a basis weight of 12 g/m$^2$, an initial thickness (at 0.5 gf/cm$^2$) of 0.15 mm, and a bulk softness of 3.7 cN in the MD and 3.3 cN in the CD was used as a base sheet. A hot-melt adhesive was applied to the base sheet in 3 mm wide stripes along the longitudinal direction (MD) at an interval of 7 mm (pitch 10 mm) in the CD. Separately, the same nonwoven fabric sheet was pressed onto a plate having a large number of grooves of prescribed depth at a prescribed pitch so as to set the sheet with as many projections as the grooves having a height of 5 mm at a pitch of 10 mm. The adhesive-applied side of the base sheet was attached thereto to prepare a topsheet having longitudinally extending projections.

The resulting topsheet, designated sample F, had an initial thickness (at 0.5 gf/cm$^2$) of 5.2 mm. The projections had a height (from the base to the top of the projections) of 5.0 mm. The width of the joints between the two sheets was 3 mm in the CD. Each projection had a semicircular profile, the width of which in the CD gradually decreased from the base toward the top.

Figure 3:
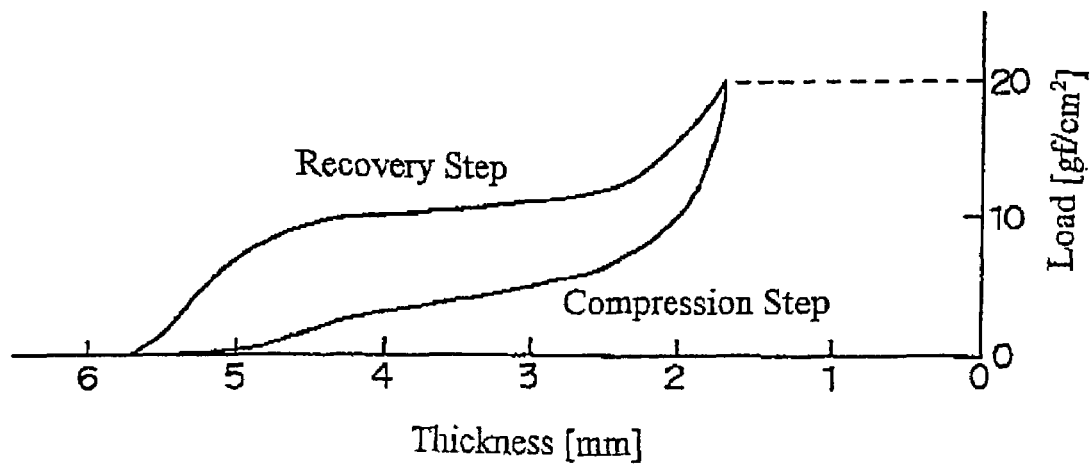
FIG. 3 shows a hysteresis loop in a compression-recovery cycle used in measuring compression characteristics of the topsheet prepared in Examples.

FIG. 3 shows the hysteresis loop of compression load vs. thickness for a compression-recovery cycle which was used for determining the compression characteristics of Sample G. In the increasing load-thickness curve, the greatest deformation (thickness change) for Δ2.5 gf/cm$^2$ appears between 2.5 gf/cm$^2$ and 20 gf/cm$^2$.

High-viscosity liquid-trapping performance:

The performance of samples A to H in trapping a high-viscosity liquid in their depressions was evaluated by the following test, in which the amount of a residual high-viscosity liquid was measured. The results obtained are shown in Table 1.

A diaper-like or sanitary napkin-like structure was fabricated from each of samples A to H as a topsheet, an intermediate absorbent sheet made of 200 g/m$^2$ of pulp and 40 g/m$^2$ of an absorbent polymer, and a waterproof backsheet. One gram of a 5% aqueous solution of carboxymethyl cellulose sodium salt as a high-viscosity liquid was poured into the structure from the topsheet side, and the structure was applied to the crotch of a human body model. The position at which the liquid had been poured corresponded to the excreting part of the model. The model with the structure fitted on was moved in a walking mode for 1 minute. The structure was removed from the model, and a stack of 10 sheets of absorbent paper was put on the area of the topsheet where the liquid had been absorbed. A load of 10 gf/cm$^2$ was put thereon for 10 seconds, and the amount of the liquid absorbed by the absorbent paper was taken as a residual amount of the liquid.

Evaluation of texture (softness):

A panel of 20 members touched samples A to H by hand, gave them scores according to the softness, and rated the texture on an A-to-D scale.

Scores of softness:

- −2: Hard
- −1: Slightly hard
- 0: Neither hard nor soft
- +1: Slightly soft
- +2: Soft Texture Rating scale:

- A: The average score given by the 20 members is higher than +0.5.
- B: The average score given by the 20 members is from 0 to +0.5.
- C: The average score given by the 20 members is from −0.5 to 0.
- D: The average score given by the 20 members is lower than −0.5.

TABLE 1

|  |  | Commercially Available Film Topsheet | | | Nonwoven Fabric Topsheet | | | Topsheet of the Invention | |
| --- | --- | --- | --- | --- | --- | --- | --- | --- | --- |
|  |  | A | B | C | D | E | F | G | H |
| 0.5 g/cm$^2$ Load | Initial Thickness $L_0$ (mm) | 0.57 | 0.64 | 0.29 | 0.40 | 1.3 | 5.2 | 5.6 | 2.9 |
| 2.5 g/cm$^2$ Load | Thickness $L_{2.5}$ (mm) | 0.52 | 0.57 | 0.28 | 0.35 | 1.13 | 3.2 | 5.4 | 2.6 |
|  | Compressive Deformation Percentage (%) | 8.8 | 10.9 | 3.4 | 12.5 | 13.1 | 38.5 | 3.6 | 10.3 |
| 5 g/cm$^2$ Load | Thickness $L_5$ (mm) | 0.49 | 0.55 | 0.26 | 0.31 | 0.93 | 2.0 | 5.2 | 2.4 |
|  | Compressive Deformation Percentage (%) | 14.0 | 14.1 | 10.3 | 22.5 | 28.5 | 61.5 | 7.1 | 17.2 |
| 20 g/cm$^2$ Load | Thickness $L_{20}$ (mm) | 0.46 | 0.46 | 0.25 | 0.22 | 0.75 | 1.6 | 1.7 | 1.4 |
|  | Compressive Deformation Percentage (%) | 19.2 | 28.1 | 13.8 | 45.0 | 42.3 | 69.2 | 69.6 | 51.7 |
| Maximum Thickness Change for Δ2.5 g/cm$^2$ (mm) | | 0.05 | 0.07 | 0.01 | 0.05 | 0.37 | 2.0 | 1.8 | 0.6 |
| Thickness $L_{R2.5}$ (mm) at 2.5 g/cm$^2$ in Recovery | | 0.48 | 0.52 | 0.25 | 0.27 | 0.68 | 1.9 | 4.4 | 2.1 |
| $D\Delta L_{R2.5}/L_{2.5}$ (%) | | 92 | 91 | 89 | 77 | 73 | 59 | 81 | 72 |
| Height (mm) of Projections | | 0.2 | — | — | 0.3 | — | 5.0 | 5.1 | 1.2 |
| Texture (Softness) | | D | D | C | B | B | B | A | A |
| Residual Amount of High-Viscosity Liquid (g) | | 0.04 | 0.04 | 0.05 | 0.04 | 0.04 | 0.05 | 0.01 | 0.01 |

The topsheet for absorbent articles according to the present invention maintains a macroscopic surface structure capable of making irritating body waste such as urine, soft tools and blood, particularly high-viscosity waste be absorbed quickly without allowing the waste to remain on the surface thereof and yet which feels soft and gives little frictional irritation to the skin, hardly causing skin troubles, such as an itch and a rash.

While the invention has been described in detail and with reference to specific examples thereof, it will be apparent that various modifications can be made therein. Such modifications are not to be regarded as a departure from the spirit and scope of the invention, and all such modifications, as would be obvious in the art, are intended to be included within the scope of the following claims.

What is claimed is:

1. A topsheet for an absorbent article which has an uneven profile formed on a surface thereof to be brought into contact with a wearer's skin, the uneven profile being flexibly deformable in conformity to the contour of the wearer's body and to the wearer's movement, and depressions of the uneven profile being capable of trapping high-viscosity excreta thereby separating the high-viscosity excreta from the wearer's skin while an absorbent article having the topsheet is worn, said uneven profile being formed by gathering an unevenness-forming sheet into a plurality of parallel hollow folds and joining the thus-folded sheet to a base sheet at only a single base at the same ends of said parallel folds of said hollow folds, wherein said hollow folds of said unevenness-forming sheet each have an Ω-shaped cross-sectional contour in their width direction, with adjacent folds not being attached to each other so as to be capable of separating high viscosity excreta from adjacent skin, and the shortest distance W3 between said adjacent parallel folds is 0 under no load being applied, said topsheet having a compressive recovery ($D\Delta L_{R2.5}/L_{2.5}$) of 70% or more as obtained from thicknesses $L_{2.5}$ and $L_{R2.5}$ according to the equation $D\Delta L_{2.5}/L_{2.5}=L_{R2.5}/L_{2.5}\times 100$, wherein $L_{2.5}$ is the thickness of the topsheet having been compressed under a load increasing up to 2.5 gf/cm$^2$, and $L_{R2.5}$ is the thickness of the topsheet having been further compressed by increasing the load to 20 gf/cm$^2$ and then relieved from compression until the load is reduced to 2.5 gf/cm$^2$, wherein said topsheet exhibits (1) a compressive deformation percentage ($C\Delta L_{2.5}$) of 0.1 to 5% based on the initial thickness when compressed under a load of 2.5 gf/cm$^2$, said compressive deformation percentage $C\Delta L_{2.5}$ being calculated from the equation: $C\Delta L_{2.5}=(L_0-L_{2.5})/L_0\times 100$, wherein $L_0$ is the initial thickness, and $L_{2.5}$ is the thickness under a load of 2.5 gf/cm$^2$, and (2) compressive deformation percentage ($C\Delta L_5$) of 5 to 20% based on the initial thickness when compressed under a load of 5 gf/cm², said compressive deformation percentage $C\Delta L_5$ being calculated from the equation $C\Delta L_5=(L_0-L_5)/L_0\times100$, wherein $L_0$ is as defined above, and $L_5$ is the thickness under a load of 5 gf/cm².

2. A topsheet for an absorbent article according to claim 1, wherein said uneven profile has a height of 0.5 to 15 mm from the base to the top thereof, and said topsheet shows (1) a maximum thickness change of 0.3 to 5 mm for a load increase by $\Delta2.5$ gf/m² when compressed in the thickness direction under a load increasing up to 20 gf/cm² and (2) a compressive deformation percentage ($C\Delta L_{20}$) of 50 to 90% based on the initial thickness when compressed under a load of 20 gf/cm² load, said compressive deformation percentage $C\Delta L_{20}$ being calculated from the equation: $C\Delta L_{20}=(L_0-L_{20})/L_0\times100$, wherein $L_0$ is the initial thickness, and $L_{20}$ is the thickness under a load of 20 gf/cm².

3. A topsheet for an absorbent article according to claim 2, wherein said maximum thickness change for a load increase by $\Delta2.5$ gf/m² occurs while the load is increased from 2.5 gf/cm² up to 20 gf/cm².

4. A topsheet for an absorbent article according to claim 1, wherein joints formed between said folded sheet and said base sheet each have a width W1 of 0.1 to 10 mm and are equally spaced at an interval W2 of 1 to 30 mm as measured between adjacent joints on said base sheet.

5. A topsheet for an absorbent article according to claim 4, wherein said unevenness-forming sheet has a bulk softness of 5 to 40 cN.

* * * * *